(12) United States Patent
Hindle et al.

(10) Patent No.: US 6,883,516 B2
(45) Date of Patent: Apr. 26, 2005

(54) METHOD FOR GENERATING AN AEROSOL WITH A PREDETERMINED AND/OR SUBSTANTIALLY MONODISPERSED PARTICLE SIZE DISTRIBUTION

(75) Inventors: Michael Hindle, Glen Allen, VA (US); Peter R. Byron, Richmond, VA (US); Rajiv Gupta, Richmond, VA (US)

(73) Assignee: Chrysalis Technologies Incorporated, Richmond, VA (US)

(*) Notice: Subject to any disclaimer, the term of this patent is extended or adjusted under 35 U.S.C. 154(b) by 32 days.

(21) Appl. No.: 09/981,739

(22) Filed: Oct. 19, 2001

(65) Prior Publication Data

US 2002/0078948 A1 Jun. 27, 2002

Related U.S. Application Data

(63) Continuation-in-part of application No. 09/560,510, filed on Apr. 27, 2000, now abandoned.

(51) Int. Cl.[7] ............................................. A61M 11/00
(52) U.S. Cl. ........................ 128/200.14; 128/203.15; 128/203.17; 128/203.26; 128/204.17; 128/200.24
(58) Field of Search ................... 128/200.14–200.24, 128/203.12, 203.5, 203.16, 203.17, 203.26, 204.17, 203.21, 203.25; 516/1–8.1; 239/1, 225.1, 10; 312/324–337, 386, 387, 391, 393, 394, 398, 396–410, 432–503; 131/329; 417/412, 474–477; 250/281, 202, 288; 73/32 R; 514/951, 957, 958; 424/43, 46

(56) References Cited

U.S. PATENT DOCUMENTS

| | | |
|---|---|---|
| 2,896,856 A | 7/1959 | Kravits |
| 3,084,698 A | 4/1963 | Smith |
| 3,157,179 A | 11/1964 | Paullus et al. |
| 3,162,324 A | 12/1964 | Houser |
| 3,431,393 A | 3/1969 | Katsuda |

(Continued)

FOREIGN PATENT DOCUMENTS

| | | |
|---|---|---|
| BE | 354004 A | 9/1928 |
| BE | 354094 A | 9/1928 |
| DE | 1036470 B1 | 8/1958 |
| EP | 0358114 A | 3/1990 |
| EP | 0642802 A2 | 5/1996 |

(Continued)

OTHER PUBLICATIONS

Written Opinion for PCT/US01/40597 dated Sep. 26, 2002.
Notification of Transmittal of the International Search Report or the Declaration for PCT/US02/30871 dated Jun. 11, 2003.

(Continued)

Primary Examiner—Glenn K. Dawson
(74) Attorney, Agent, or Firm—Burns, Doane, Swecker & Mathis, LLP (57) ABSTRACT

A method is provided for generating an aerosol. The method includes preparing a solution formed of a first component in a liquid component such that after volatilization of the liquid component by passing the solution through a flow passage while heating the solution, an aerosol is formed having a predetermined particle size distribution of the first component, wherein the solution is prepared such that the amount of the first component therein is sufficient to achieve the predetermined particle size distribution of the first component. The method also includes passing the solution through the flow passage while heating the solution to a temperature sufficient to volatilize the liquid component, wherein the flow passage comprises an outlet through which the first component and the volatilized liquid component flow, and wherein an aerosol is formed.

45 Claims, 3 Drawing Sheets

U.S. PATENT DOCUMENTS

| | | | |
|---|---|---|---|
| 3,486,663 A | 12/1969 | Humphrey | |
| 3,658,059 A | 4/1972 | Steil | |
| 3,716,416 A | 2/1973 | Adlhart et al. | |
| 3,750,961 A | 8/1973 | Franz | |
| 3,847,304 A | 11/1974 | Cohen | |
| 3,859,398 A | 1/1975 | Havstad | |
| 3,902,635 A | 9/1975 | Jinotti | |
| 3,903,883 A | 9/1975 | Pecina et al. | |
| 3,904,083 A | 9/1975 | Little | |
| 3,967,001 A | 6/1976 | Almaula et al. | |
| 3,987,941 A | 10/1976 | Blessing | |
| 3,993,246 A | 11/1976 | Erb et al. | |
| 4,042,153 A | 8/1977 | Callahan et al. | |
| 4,060,082 A | 11/1977 | Lindberg et al. | |
| 4,077,542 A | 3/1978 | Petterson | |
| 4,161,282 A | 7/1979 | Erb et al. | |
| 4,162,501 A | 7/1979 | Mitchell et al. | |
| 4,215,708 A | 8/1980 | Bron | |
| 4,231,492 A | 11/1980 | Rios | |
| 4,258,073 A | 3/1981 | Payne | |
| 4,261,356 A | 4/1981 | Turner et al. | |
| 4,289,003 A | 9/1981 | Yang | |
| 4,291,838 A | 9/1981 | Williams | |
| 4,303,083 A | 12/1981 | Burruss, Jr. | |
| 4,383,171 A | 5/1983 | Sinha et al. | |
| 4,391,308 A | 7/1983 | Steiner | |
| 4,395,303 A | 7/1983 | Weir | |
| 4,433,797 A | 2/1984 | Galia | |
| 4,471,892 A | 9/1984 | Coleman | |
| 4,484,577 A * | 11/1984 | Sackner et al. | 128/203.28 |
| 4,512,341 A | 4/1985 | Lester | |
| 4,575,609 A | 3/1986 | Fassel et al. | |
| 4,627,432 A | 12/1986 | Newell et al. | |
| 4,649,911 A | 3/1987 | Knight et al. | |
| 4,682,010 A | 7/1987 | Drapeau et al. | |
| 4,695,625 A | 9/1987 | Macdonald | |
| 4,700,657 A | 10/1987 | Butland | |
| 4,730,111 A | 3/1988 | Vestal et al. | |
| 4,735,217 A | 4/1988 | Gerth et al. | |
| 4,744,932 A | 5/1988 | Browne | |
| 4,749,778 A | 6/1988 | Fukuzawa et al. | |
| 4,762,995 A | 8/1988 | Browner et al. | |
| 4,776,515 A | 10/1988 | Michalchik | |
| 4,790,305 A | 12/1988 | Zoltan et al. | |
| 4,811,731 A | 3/1989 | Newell et al. | |
| 4,819,625 A | 4/1989 | Howe | |
| 4,819,834 A | 4/1989 | Thiel | |
| 4,829,996 A | 5/1989 | Noakes et al. | |
| 4,837,260 A | 6/1989 | Sato et al. | |
| 4,848,374 A | 7/1989 | Chard et al. | |
| 4,871,115 A | 10/1989 | Hessey | |
| 4,871,623 A | 10/1989 | Hoopman et al. | |
| 4,877,989 A | 10/1989 | Drews et al. | |
| 4,911,157 A | 3/1990 | Miller | |
| 4,922,901 A | 5/1990 | Brooks et al. | |
| 4,926,852 A | 5/1990 | Zoltan et al. | |
| 4,935,624 A | 6/1990 | Henion et al. | |
| 4,941,483 A | 7/1990 | Ridings et al. | |
| 4,947,875 A | 8/1990 | Brooks et al. | |
| 4,974,754 A | 12/1990 | Wirz | |
| 4,982,097 A | 1/1991 | Slivon et al. | |
| 4,992,206 A | 2/1991 | Waldron | |
| 5,021,802 A | 6/1991 | Allred | |
| 5,044,565 A | 9/1991 | Alexander | |
| 5,056,511 A | 10/1991 | Ronge | |
| 5,060,671 A | 10/1991 | Counts et al. | |
| 5,063,921 A | 11/1991 | Howe | |
| 5,096,092 A | 3/1992 | Devine | |
| 5,125,441 A | 6/1992 | Mette | |
| 5,133,343 A | 7/1992 | Johnson, IV et al. | |
| 5,134,993 A | 8/1992 | van der Linden et al. | |
| 5,135,009 A | 8/1992 | Müller et al. | |
| 5,144,962 A | 9/1992 | Counts et al. | |
| 5,151,827 A | 9/1992 | Ven et al. | |
| 5,178,305 A | 1/1993 | Keller | |
| 5,184,776 A | 2/1993 | Minier | |
| 5,217,004 A | 6/1993 | Blasnik et al. | |
| 5,226,441 A | 7/1993 | Dunmire et al. | |
| 5,228,444 A | 7/1993 | Burch | |
| 5,230,445 A | 7/1993 | Rusnak | |
| 5,231,983 A | 8/1993 | Matson et al. | |
| 5,259,370 A | 11/1993 | Howe | |
| 5,290,540 A | 3/1994 | Prince et al. | |
| 5,298,744 A | 3/1994 | Mimura et al. | |
| 5,299,565 A | 4/1994 | Brown | |
| 5,322,057 A | 6/1994 | Raabe et al. | |
| 5,327,915 A | 7/1994 | Porenski et al. | |
| 5,342,180 A | 8/1994 | Daoud | |
| 5,342,645 A | 8/1994 | Eisele et al. | |
| 5,349,946 A | 9/1994 | McComb | |
| 5,395,445 A | 3/1995 | Bohanan | |
| 5,421,489 A | 6/1995 | Holzner, Sr. et al. | |
| 5,462,597 A | 10/1995 | Jubran | |
| 5,474,059 A | 12/1995 | Cooper | |
| 5,515,842 A | 5/1996 | Ramseyer et al. | |
| 5,522,385 A | 6/1996 | Lloyd et al. | |
| 5,556,964 A | 9/1996 | Hofstraat et al. | |
| 5,564,442 A | 10/1996 | MacDonald et al. | |
| 5,565,677 A | 10/1996 | Wexler | |
| 5,575,929 A | 11/1996 | Yu et al. | |
| 5,585,045 A | 12/1996 | Heinonen et al. | |
| 5,617,844 A | 4/1997 | King | |
| 5,642,728 A | 7/1997 | Andersson et al. | |
| 5,674,860 A | 10/1997 | Carling et al. | |
| 5,682,874 A | 11/1997 | Grabenkort et al. | |
| 5,730,158 A | 3/1998 | Collins et al. | |
| 5,743,251 A | 4/1998 | Howell et al. | |
| 5,756,995 A | 5/1998 | Maswadeh et al. | |
| 5,765,724 A | 6/1998 | Amberg et al. | |
| 5,819,726 A * | 10/1998 | Rubsamen et al. | 128/200.14 |
| 5,823,178 A | 10/1998 | Lloyd et al. | |
| 5,839,430 A | 11/1998 | Cama | |
| 5,855,202 A | 1/1999 | Andrade | |
| 5,855,913 A * | 1/1999 | Hanes et al. | 424/489 |
| 5,856,671 A | 1/1999 | Henion et al. | |
| 5,863,652 A | 1/1999 | Matsumura et al. | |
| 5,869,133 A | 2/1999 | Anthony et al. | |
| 5,872,010 A | 2/1999 | Karger et al. | |
| 5,878,752 A | 3/1999 | Adams et al. | |
| 5,881,714 A | 3/1999 | Yokoi et al. | |
| 5,906,202 A | 5/1999 | Schuster et al. | |
| 5,914,122 A | 6/1999 | Otterbeck et al. | |
| 5,932,249 A | 8/1999 | Gruber et al. | |
| 5,932,315 A | 8/1999 | Lum et al. | |
| 5,934,272 A | 8/1999 | Lloyd et al. | |
| 5,934,273 A | 8/1999 | Andersson et al. | |
| 5,944,025 A | 8/1999 | Cook et al. | |
| 5,954,979 A | 9/1999 | Counts et al. | |
| 5,957,124 A | 9/1999 | Lloyd et al. | |
| 5,958,378 A | 9/1999 | Waldrep et al. | |
| 5,970,973 A | 10/1999 | Gonda et al. | |
| 5,970,974 A | 10/1999 | Van Der Linden et al. | |
| 5,978,548 A | 11/1999 | Holmstrand et al. | |
| 5,993,633 A | 11/1999 | Smith et al. | |
| 6,014,970 A | 1/2000 | Ivri et al. | |
| 6,053,176 A | 4/2000 | Adams et al. | |
| 6,054,032 A | 4/2000 | Haddad et al. | |
| 6,069,214 A | 5/2000 | McCormick et al. | |
| 6,069,219 A | 5/2000 | McCormick et al. | |
| 6,070,575 A | 6/2000 | Gonda et al. | |
| 6,071,428 A | 6/2000 | Franks et al. | |

| | | |
|---|---|---|
| 6,076,522 A | 6/2000 | Dwivedi et al. |
| 6,077,543 A | 6/2000 | Gordon et al. |
| 6,080,721 A | 6/2000 | Patton |
| 6,085,740 A | 7/2000 | Ivri et al. |
| 6,085,753 A | 7/2000 | Gonda et al. |
| 6,089,228 A | 7/2000 | Smith et al. |
| 6,095,153 A | 8/2000 | Kessler et al. |
| 6,098,615 A | 8/2000 | Lloyd et al. |
| 6,098,620 A | 8/2000 | Lloyd et al. |
| 6,103,270 A | 8/2000 | Johnson et al. |
| 6,116,516 A | 9/2000 | Gañán-Calvo |
| 6,116,893 A | 9/2000 | Peach |
| 6,119,953 A | 9/2000 | Gañán-Calvo et al. |
| 6,123,068 A | 9/2000 | Lloyd et al. |
| 6,123,936 A | 9/2000 | Platz et al. |
| 6,131,567 A | 10/2000 | Gonda et al. |
| 6,131,570 A | 10/2000 | Schuster et al. |
| 6,136,346 A | 10/2000 | Eljamal et al. |
| 6,138,668 A | 10/2000 | Patton et al. |
| 6,155,268 A | 12/2000 | Takeuchi |
| 6,158,431 A | 12/2000 | Poole |
| 6,158,676 A | 12/2000 | Hughes |
| 6,159,188 A | 12/2000 | Laibovitz et al. |
| 6,164,630 A | 12/2000 | Birdsell et al. |
| 6,165,463 A | 12/2000 | Platz et al. |
| 6,167,880 B1 | 1/2001 | Gonda et al. |
| 6,174,469 B1 | 1/2001 | Gañán-Calvo |
| 6,182,712 B1 | 2/2001 | Stout et al. |
| 6,187,214 B1 | 2/2001 | Gañán-Calvo |
| 6,187,344 B1 | 2/2001 | Eljamal et al. |
| 6,189,803 B1 | 2/2001 | Gañán-Calvo |
| 6,192,882 B1 | 2/2001 | Gonda |
| 6,197,835 B1 | 3/2001 | Gañán-Calvo |
| 6,205,999 B1 | 3/2001 | Ivri et al. |
| 6,206,242 B1 | 3/2001 | Amberg et al. |
| 6,207,135 B1 | 3/2001 | Rössling et al. |
| 6,223,746 B1 | 5/2001 | Jewett et al. |
| 6,230,706 B1 | 5/2001 | Gonda et al. |
| 6,231,851 B1 | 5/2001 | Platz et al. |
| 6,234,167 B1 | 5/2001 | Cox et al. |
| 6,234,402 B1 | 5/2001 | Gañán-Calvo |
| 6,235,177 B1 | 5/2001 | Borland et al. |
| 6,250,298 B1 | 6/2001 | Gonda et al. |
| 6,257,233 B1 | 7/2001 | Burr et al. |
| 6,258,341 B1 | 7/2001 | Foster et al. |
| 6,263,872 B1 | 7/2001 | Schuster et al. |
| 6,267,155 B1 | 7/2001 | Parks et al. |
| 6,275,650 B1 | 8/2001 | Lambert |
| 6,276,347 B1 | 8/2001 | Hunt |
| 6,284,525 B1 | 9/2001 | Mathies et al. |
| 6,288,360 B1 | 9/2001 | Beste |
| 6,290,685 B1 | 9/2001 | Insley et al. |
| 6,294,204 B1 | 9/2001 | Rössling et al. |
| 6,295,986 B1 | 10/2001 | Patel et al. |
| 6,318,361 B1 | 11/2001 | Sosiak |
| 6,585,958 B1 * | 7/2003 | Keller et al. ............ 424/45 |
| 6,601,776 B1 | 8/2003 | Oljaca et al. |
| 2001/0032647 A1 | 10/2001 | Schuster et al. |
| 2001/0036495 A1 * | 11/2001 | Ganan-Calvo ............ 426/231 |
| 2001/0043906 A1 * | 11/2001 | Vlasselaer et al. ............ 424/43 |
| 2002/0086852 A1 * | 7/2002 | Cantor et al. ............ 514/54 |
| 2002/0102312 A1 * | 8/2002 | Tepper et al. ............ 424/490 |

FOREIGN PATENT DOCUMENTS

| | | |
|---|---|---|
| FR | 667979 A | 10/1929 |
| HU | 168128 B | 11/1977 |
| HU | 216121 B | 3/1991 |
| HU | 207457 A | 4/1993 |
| HU | P953409 | 6/1994 |
| WO | 94/09842 A | 5/1994 |
| WO | 98/17131 | 4/1998 |

OTHER PUBLICATIONS

Written Opinion dated Dec. 24, 2003 for PCT/US02/30871.

Barry, P.W. et al. "In Vitro Comparison of the Amount of Salbutamol Available for Inhalation From Different Formulations Used with Different Spacer Devices" Eur Respir J 1997; 10: 1345–1348.

Byron, Peter R. Ph.D., Chairman, "Recommendations of the USP Advisory Panel on Aerosols on the USP General Chapters on Aerosols (601) and Uniformity of Dosage Units (905)", Pharamacopeial Forum, vol. 20, No. 3, pp. 7477–7505, May–Jun. 1994 (023).

Hindle, Michael et al., "High Efficiency Aerosol Production Using the Capillary Aerosol Generator" PharmSci 1998; 1: (1: suppl) S211.

Hindle, Michael et al., "High Efficiency Fine Particle Generation Using Novel Condensation Technology", Respiratory Drug Delivery VI (eds Dalby, R.N., Byron, P.R. & Farr, S.J.) Interpharm Press, Buffalo Grove, IL 1998 pp 97–102.

Hou, Shuguang et al. *Solution Stability of Budenoside in Novel Aerosol Formulations* Abstract No. 2582, Solid State Physical Pharmacy, Nov. 17, 1998, p. S–307.

Kousaka, Yasuo et al., "Generation of Aerosol Particles by Boiling of Suspensions", Aerosol Science and Technology, 21:236–240 (1994) (023).

Morén, Folke "Drug Deposition of Pressurized Inhalation Aerosols I. Influence of Actuator Tube Design" AB Draco (Subsidiary of AB Astra, Sweden) Research and Development Laboratories Pack, S–221 01 Lund (Sweden), International Journal of Pharmaceutrics, 1 (1978) 205–212.

Newman, Stephen P. et al. "Deposition of Pressurized Suspension Aerosols Inhaled Through Extension Devices[1–3n]" Am Rev Respir Dis 1981; 124:317–320.

Roth, G. et al. High Performance Liquid Chromatographic Determination of Epimers, Impurities, and Content of the Glucocorticoid Budesonide and Preparation of Primary Standard, Journal of Pharmaceutical Sciences, vol. 69, No. 7, pp. 766–770, Jul. 1980.

\* cited by examiner

METHOD FOR GENERATING AN AEROSOL WITH A PREDETERMINED AND/OR SUBSTANTIALLY MONODISPERSED PARTICLE SIZE DISTRIBUTION

CROSS-REFERENCE TO RELATED APPLICATION

This application is a continuation-in-part application of U.S. patent application Ser. No. 09/560,510, filed on Apr. 27, 2000 now abandoned, the entire contents of which are incorporated herein by reference.

FIELD OF THE INVENTION

The present invention relates to methods for generating aerosols, and more particularly to achieving a predetermined and/or a substantially monodispersed particle size distribution of at least one component in the aerosol.

BACKGROUND OF THE INVENTION

An aerosol typically is comprised of finely divided particles of a liquid and/or solid and is useful in a wide variety of applications. An aerosol can be used to administer a medicament, for example, by being inhaled into the lungs of an animal or human. Other applications of aerosols include, for example, instrument calibration, inhalation toxicology studies, air filter testing, nuclear safety analysis, and the delivery of scented materials, paints and lubricants.

In the delivery of a medicament to the lungs of an animal or human, the location in the lungs which should be treated with such a medicament at least depends on the type of ailment being treated and the type of medicament being used. The particle size distribution and the uniformity of an aerosol typically control or contribute to the location at which the aerosol particles settle in the lungs. As used herein, the term "particle size distribution" relates to the mass distribution of a material over a range of particle sizes of the material. The uniformity of an aerosol relates to the degree of dispersion of the mass distribution of a material over a range of particle sizes of the material.

Providing aerosol particles having an excessively large particle size distribution can have an adverse effect on the administration of the medicament. For example, aerosol particles having large particle size distributions can be deposited in the mouth and/or pharynx of a recipient, rather than inhaled into the lungs. On the other hand, providing aerosol particles having an excessively small particle size distribution can also have an adverse effect on the administration of the medicament, for example, because such small particles are sometimes exhaled prior to settling in the lungs.

Providing aerosol particles having an excessively broad range of particle sizes can have an adverse effect on the administration of the medicament. For example, aerosol particles with an excessively broad range of particle sizes are generally deposited throughout the lung or multiple parts of the lung, rather than a specific site in the lung. Thus, to effectively deposit a medicament in the lungs, it can be important to obtain an aerosol having a predetermined and sufficiently uniform particle size distribution which is suitable for treating a particular ailment using a particular medicament.

The particle size distribution of an aerosol or a component that is present in the aerosol can be measured by determining the mass median aerosol diameter (MMAD) thereof. The MMAD of an aerosol is the mass median diameter of the aerosol particles. The MMAD of a component present in an aerosol is the mass median diameter of the aerosol particles containing the component to be measured.

As discussed above, the uniformity of a particle size distribution can also affect the placement of the aerosol deposition in the lungs. The uniformity of a particle size distribution of an aerosol or a component that is present in the aerosol can be measured by determining the geometric standard deviation (GSD) thereof. The GSD of an aerosol or a component that is present in the aerosol is calculated as the ratio of the observed particle size at the $84^{th}$ percentile divided by the observed particle size at the $50^{th}$ percentile on a cumulative percent mass undersize distribution. The terms "monodispersed" and "polydispersed" as used herein relate to the uniformity of the particle size distribution of the aerosol. The lower the GSD is of an aerosol, the more "monodispersed" the particle size distribution is. Similarly, the higher the GSD is of an aerosol, the more "polydispersed" the particle size distribution is. For example, monodispersed particle size distributions typically include aerosols having a GSD of about 2 or less and polydispersed particle size distributions typically include aerosols having a GSD of about 3 or more.

In view of the foregoing, it is desirable to provide a means for achieving a predetermined and/or substantially monodispersed particle size distribution of an aerosol. It is also desirable to provide a means for achieving a sufficiently small particle size distribution of an aerosol which allows for the deep penetration of the aerosol into the lungs and for the treatment of an ailment requiring such deep penetration. It is further desirable to provide a means for achieving a sufficiently large particle size distribution which allows for the central deposition of the aerosol into the lungs and for the treatment of an ailment requiring such central deposition. One or more of these attributes can be achieved by the methods described herein.

SUMMARY OF THE INVENTION

According to one aspect of the present invention, a method is provided for generating an aerosol. The method includes preparing a solution formed of a first component in a liquid component such that after volatilization of the liquid component by passing the solution through a flow passage while heating the solution, an aerosol is formed having a predetermined particle size distribution of the first component, wherein the solution is prepared such that the amount of the first component therein is sufficient to achieve the predetermined particle size distribution of the first component. The method also includes passing the solution through the flow passage while heating the solution to a temperature sufficient to volatilize the liquid component, wherein the flow passage comprises an outlet through which the volatilized liquid component and the first component flow, and wherein an aerosol is formed.

According to another aspect of the present invention, a method is provided for generating an aerosol. The method includes preparing a solution formed of a first component in a liquid component such that after volatilization of the liquid component by passing the solution through a flow passage while heating the solution, an aerosol is formed having a predetermined and substantially monodispersed particle size distribution of the first component, wherein the solution is prepared such that the boiling point of the liquid component is sufficient to achieve the predetermined and substantially monodispersed particle size distribution of the first component. The method also includes passing the solution through the flow passage while heating the solution to a temperature sufficient to volatilize the liquid component, wherein the flow passage comprises an outlet through which the volatilized liquid component and the first component flow, and wherein an aerosol is formed.

According to another aspect of the present invention, a method is provided for generating an aerosol. The method includes preparing a solution of a first component in a liquid component such that after volatilization of the liquid component by passing the solution through a flow passage while heating the solution, an aerosol is formed having a predetermined and substantially monodispersed particle size distribution of the first component, wherein the solution is prepared such that the amount of the first component therein and the boiling point of the liquid component are sufficient to achieve the predetermined and substantially monodispersed particle size distribution of the first component. The method also includes passing the solution through the flow passage while heating the solution to a temperature sufficient to volatilize the liquid component, wherein the flow passage comprises an outlet through which the first component and the volatilized liquid component flow, and wherein aerosol particles are formed.

According to another aspect of the present invention, a method is provided for controlling a particle size distribution of an aerosol. The method includes preparing a solution comprising a first component in a liquid component, wherein the solution achieves a predetermined particle size distribution of the first component upon volatilization of the solution by passing the solution through a flow passage while heating the solution.

According to a further aspect of the present invention, a method is described for providing a monodispersed particle size distribution of an aerosol. The method includes preparing a solution comprising a first component in a liquid component, wherein the solution achieves a monodispersed particle size distribution of the first component upon volatilization of the solution by passing the solution through a flow passage while heating the solution.

BRIEF DESCRIPTION OF THE DRAWINGS

The features and advantages of the present invention are well understood by reading the following detailed description in conjunction with the drawings in which like numerals indicate similar elements and in which.

DETAILED DESCRIPTION

The present invention relates to methods for generating an aerosol. The methods can be used to administer a medicament to the lungs of an animal or human. For example, the methods can be used to treat respiratory ailments such as, for example, asthma, emphysema, chronic obstructive airway disease, bronchitis and cystic fibrosis. The present methods can also be used in the treatment of other ailments and diseases such as, for example, to administer pain relief medicaments (analgesics) and to treat diabetes. Advantageously, by employing the instant methods, the particle size distribution of a component in a solution to be aerosolized can be controlled. In addition, the instant methods can also achieve a monodispersed particle size distribution of a component in a solution to be aerosolized.

Figure 1:
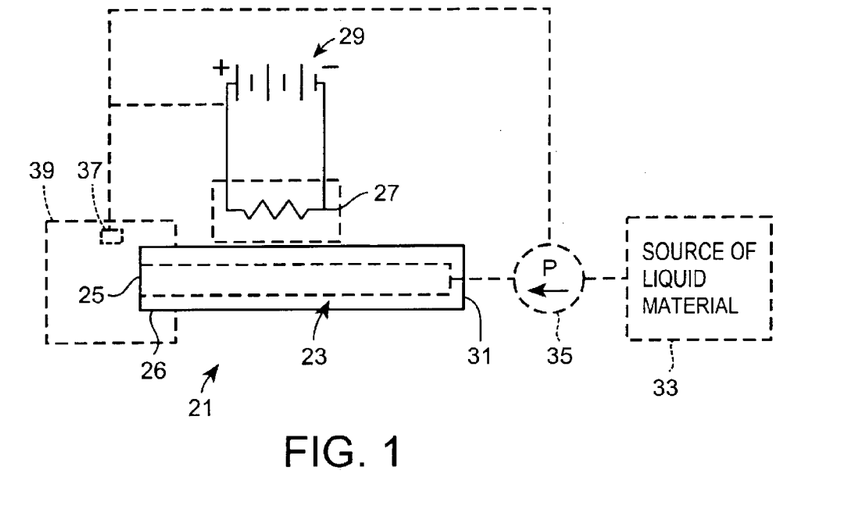
FIG. 1 is a schematic view of an aerosol generator according to an exemplary embodiment of the present invention.

An exemplary aerosol generator 21 which can be used in the instant methods is schematically shown in FIG. 1. The aerosol generator 21 includes a flow passage 23 having an outlet 25. A heater 27 can be positioned adjacent to at least a portion of the flow passage 23, preferably in a manner which provides a heated zone around the flow passage and which maximizes heat transfer throughout the heated zone. The heater 27 can be connected to a power supply 29, preferably a D.C. power supply such as a battery.

A solution formed of a first component in a liquid component can be introduced to the flow passage 23. The solution is suitable for aerosolization by an aerosol generator such as the aerosol generator 21 shown in FIG. 1. The solution is preferably a substantially homogeneous mixture of the first component and the liquid component. Typically, the solution is formed by adding the first component to and/or mixing the first component with the liquid component. Other methods for combining the materials which are known to those skilled in the art can be used.

Preferably, the first component is useful for treating a disease or ailment such as a respiratory ailment. For example, the first component can include budesonide and/or albuterol. Other materials known in the art which are readily added to or dissolved in a liquid can also be used. In the examples that follow, other components are used including deoxycorticosterone, benzil and phenyl salicylate, to exemplify that components having various physical and chemical properties can be used in the present methods. Prior to forming the solution, the first component can be in a solid or liquid phase, preferably in a solid phase. In the case of a solid material, the first component can be dissolved in the liquid component and/or suspended in the liquid component.

The liquid component preferably can be volatilized by passing the solution containing the liquid component through a flow passage of an aerosol generator and heating the flow passage. The liquid component can have medicinal properties and/or can operate as a vehicle for the first component. For example, in an exemplary embodiment, the liquid component operates as a vehicle for the first component and the first component is a medicament. The liquid component can include, for example, water and/or an alcohol such as, for example, propylene glycol, ethylene glycol, dipropylene glycol, diethylene glycol, triethylene glycol, tetraethylene glycol, oleyl alcohol, ethanol and mixtures thereof. The liquid preferably includes propylene glycol.

The heater 27 heats the portion of the flow passage 23 to a sufficient temperature to volatilize the liquid component and optionally the first component. The heater preferably heats the liquid component at least to about the boiling point of the liquid component and preferably maintains the surface temperature of the flow passage 23 below 400° C. The volatilized liquid component flows out of the outlet 25 of the flow passage 23 and typically condenses after mixing with ambient air to form aerosol particles.

Upon volatilization of the liquid component, the first component can also be volatilized or remain in a solid or liquid state. Preferably, at least some of the first component volatilizes as a result of the solution being heated. The first component typically flows out of the outlet 25 of the flow passage 23 contemporaneously with the volatilized liquid component but can also flow out of the outlet 25 after the volatilized liquid flows out of the outlet. The contemporaneous flow of the first component and the liquid component out of the outlet 25 is referred to herein as "co-evaporation." Achieving co-evaporation can depend on various parameters such as, for example, the types and amounts of the first component and liquid component that are used, the temperature of the flow passage 23 and the flow rate of the solution.

According to an exemplary embodiment, a solution is prepared such that the amount of the first component therein is sufficient to achieve a predetermined particle size distribution of the first component and/or the liquid component upon aerosolization of the solution. Advantageously, reducing the amount of the first component in the solution generally has the effect of increasing the MMAD and/or the degree of uniformity of the first component upon aerosolization of the solution. On the other hand, increasing the amount of the first component in the solution generally has the opposite effect, i.e., it decreases the MMAD of the first component upon aerosolization of the solution. The amount of the first component in the solution typically is from about 0.03 to 50% by weight of the solution. The effects of adjusting the concentration of the first component which are described above generally relate to solutions which contain small amounts of the first component in the liquid component, particularly in the range of 0.03 to 1% by weight, preferably less than about 0.5% by weight, and even more preferably less than about 0.1% by weight, but can also be applied to solutions which contain larger amounts of the first component.

The amount of the first component can also be sufficient to achieve a substantially monodispersed particle size distribution of the first component. For example, the GSD of the particle size distribution of the first component can be less than or equal to 2.

The desired particle size distribution and/or the degree of uniformity of the aerosolized first component and/or liquid component typically depend on the specific application of the aerosol. That is, the desired particle size distribution and/or the degree of uniformity generally depend on the particular disease or ailment that is desired to be treated and the particular material that is used to treat the disease or ailment. In the treatment of respiratory diseases and ailments such as, for example, asthma, chronic obstructive airway disease, bronchitis and emphysema, it is typically desirable to provide medicament aerosol particles which have a relatively medium-sized or large-sized MMAD, for example, typically less than 3 $\mu$m, preferably from about 1.0 to 3.0 $\mu$m, more preferably from about 0.3 to 2 $\mu$m, and a substantially monodispersed distribution. In the treatment of systemic diseases and ailments, it is generally desirable to provide aerosol particles having a relatively small-sized MMAD, for example, about 0.5 $\mu$m.

According to another aspect of the present invention, a predetermined and/or substantially monodispersed particle size distribution of the first component and/or the liquid component can be achieved by preparing the solution such that the boiling point of the liquid component is sufficient to achieve the predetermined and/or a substantially monodispersed particle size distribution. The solution can also be prepared such that other properties of the liquid component such as, for example, the viscosity, the specific heat capacity, the vaporization enthalpy and hydrogen bonding properties thereof, are sufficient to achieve the predetermined and substantially monodispersed particle size distribution. Applicants have surprisingly found that preparing a solution containing a liquid component having an increased boiling point typically increases the degree of uniformity of the particle size distribution of the aerosolized first component. For example, the GSD of the particle size distribution of the first component can be less than or equal to about 2 such as, for example, from about 1.5 to 2. On the other hand, using a liquid component with a lower boiling point generally has the opposite effect, i.e., the particle size distribution of the first component typically becomes more bimodal and/or polydispersed upon aerosolization of the solution. As shown in the following examples, some liquid components may not follow this trend, and while not wishing to be bound by theory, Applicants hypothesize that other properties such as physical and/or chemical properties of the liquid component also contribute to the particle size distribution and/or uniformity thereof.

The liquid component preferably is aerosolized by heating the solution containing the liquid component to a temperature at or above the boiling point of the liquid component, for example at a temperature not less than 400° C. in certain applications. Thus, the temperature of the flow passage of the aerosol generator during aerosolization generally at least depends on the boiling point of the liquid component.

In certain applications, it can be beneficial to provide an aerosol wherein the first component aerosol particles and the liquid component aerosol particles have similar or equal MMADs. This phenomena is referred to herein as "co-condensation." According to one aspect of the present invention, the ratio of the MMAD of the first component aerosol particles to the MMAD of the liquid component aerosol particles is greater than or equal to 0.75 as a result of using a solution which is prepared in accordance with the present invention. In other applications, co-condensation may not be preferred and it may be desirable to obtain a ratio of the MMAD of the first component aerosol particles to the MMAD of the liquid component aerosol particles to be less than or equal to 0.75.

The parameters relating to the operation of the aerosol generator can affect the particle size distribution of the first component aerosol particles and/or the liquid component aerosol particles. Such parameters include, for example, the amount of material that is vaporized per second; the amount of entrained air per unit weight of the vaporized material; the exit velocity of the vaporized material flowing from the outlet of the aerosol generator; the temperature of the flow passage; and the shape of the flow passage.

Referring to FIG. 1, the flow passage 23 of the aerosol generator 21 typically comprises an enclosed volume which opens to an inlet and/or an outlet 25. The flow passage 23 can be formed into any shape through which a fluid or a mixture of a fluid and a solid may pass. The flow passage 23 can have any desired geometry. A preferred shape of a cross-sectional profile of the flow passage 23 is a circular hole of uniform diameter. Other cross-sectional flow passage shapes include non-circular shapes such as triangular, square, rectangular, oval or other shapes. The cross section of the hole need not be uniform. The flow passage 23 can extend rectilinearly or non-rectilinearly and may be a single flow passage or a multi-path flow passage.

The flow passage 23 preferably is of "capillary dimensions." A flow passage of capillary dimensions permits volatilization of substantially all of the liquid present in the flow passage when the flow passage is heated. For example, the cross-sectional area of a flow passage of capillary dimensions typically is sufficiently small to enable the efficient heating of the solution present in the flow passage.

In an exemplary embodiment, the flow passage 23 comprises a tube. The flow passage 23 is preferably about 10 to 50 mm long, more preferably about 44 mm. The flow passage 23 preferably has an inside diameter of between 0.05 and 0.53 millimeter and a gauge of about 26 to 32. The wall thickness is preferably about 0.0025 inch (0.064 mm). The dimensions of the flow passage 23 typically depend on many factors including, for example, the overall size of the aerosol generator desired, the material(s) to be volatilized, the amount of aerosol to be delivered, and the like. The aerosol generator can optionally include a sleeve 26 disposed proximate to the outlet 25 of the flow passage 23.

The flow passage 23 can be formed of a ceramic or glass material. Preferably, the flow passage is formed of fused silica or an aluminum silicate. Other substantially non-reactive materials capable of withstanding repeated heating cycles and generated pressures and having suitable heat conduction properties can also be used such as, for example, stainless steel.

The heater 27 is preferably an electrical resistance heater. According to a preferred embodiment, the heater 27 is a heater wire having an outside diameter of 0.008 inches, a resistance of 13.1 ohms per foot, and a specific heat of 0.110 BTU/lb ° F. The composition of the heater wire is preferably 71.7% iron, 23% chromium, and 5.3% aluminum. Such a heater wire is available from Kanthal Furnace Products, located in Bethel, Conn.

The power supply 29 is sized to provide sufficient power for the heating element 27 that heats a portion or the entire flow passage 23. The power supply 29 is preferably replaceable and rechargeable and may include devices such as a capacitor and/or a battery. For portable applications, the power supply is, in a presently preferred embodiment, a replaceable, rechargeable battery such as four nickel cadmium battery cells connected in series with a total, non-loaded voltage of approximately 4.8 to 5.6 volts. The characteristics required of the power supply 29 are, however, selected in view of the characteristics of other components of the aerosol generator 21, particularly the characteristics of the heater 27. One power supply that has been found to operate successfully in generating an aerosol from liquid propylene glycol is operated continuously at approximately 2.5 Volts and 0.8 Amps.

Figure 2:
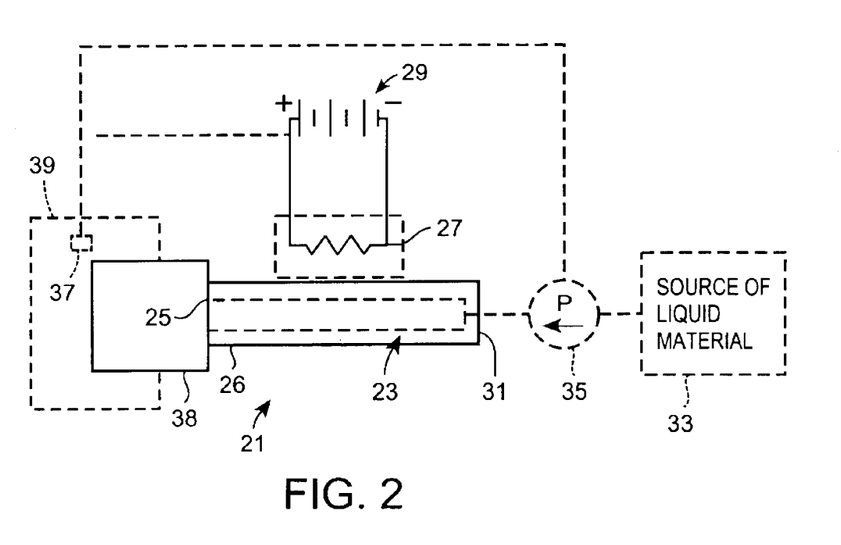
FIG. 2 is a schematic view of an aerosol generator according to an alternate embodiment of the present invention.

The mouthpiece 39 can be disposed proximate the open end 25 of the flow passage 23 and facilitates complete mixing of the volatilized liquid with cooler ambient air such that the volatilized liquid condenses to form particles. For medicament delivery applications, the mouthpiece 39 is preferably designed to permit passage of approximately 60–100 liters of air per minute without substantial resistance, such a flow rate being the normal flow for inhalation from an inhaler. Of course, the mouthpiece 39, if provided, may be designed to pass more or less air, depending upon the intended application of the aerosol generator and other factors, such as consumer preferences. A preferred mouthpiece for a hand held asthma inhaler is approximately 1 inch in diameter and between 1.5 and 2 inches in length, with the open end 25 of the flow passage 23 centered at an end of the mouthpiece. Referring to FIG. 2, depending on the desired aerosol droplet size, a spacer chamber 38 can be added at the open end 25 of the flow passage 23 before the mouthpiece 39. The spacer chamber 38 can have the effect of increasing or decreasing the particle size distribution of the aerosol.

Other embodiments and aspects of the aerosol generator that can be used in the instant methods are described in U.S. application Ser. No. 09/560,510, the contents of which are incorporated by reference.

The aerosol can be generated intermittently, e.g., on demand, or continuously. When it is desired to generate an intermittent aerosol, the solution can be supplied to the portion of the flow passage 23 proximate the heater 27 each time that it is desired to generate an aerosol. Preferably, the solution flows from a solution source 33 to a portion of the flow passage 23 proximate the heater 27, such as by being pumped by a pump 35 (shown by dotted lines). The intermittent generation and continuous generation of aerosols which can be used in the present invention are discussed in greater detail in U.S. application Ser. No. 09/560,510, the contents of which are incorporated by reference.

In the following examples, the trends observed for the exemplary first components and liquid components are expected to hold true for other combinations of materials, although those skilled in the art will recognize that altering variables such as the flow rates and temperatures in the aerosol generator may well enable further manipulations of particle size distributions beyond those noted here.

EXAMPLES

Aerosols were generated from various solutions by introducing the solutions to an aerosol generator. The MMAD and GSD of the aerosols were measured to determine the effects of (1) varying the concentration of the first component in the solution and (2) varying the boiling point of the liquid component.

The aerosol generator used in the examples includes a 26 gauge stainless steel capillary tube flow passage which had an inside diameter of 0.27 mm and a length of 44 mm. A syringe pump was used to supply the solution to the capillary tube flow passage. The syringe pump which was used was a Model 44 syringe pump, obtained from Harvard Apparatus located in South Natich, Mass. The syringe needle that was used was a Microliter No. 750, obtained from Hamilton Co. located in Reno, Nev. A Model 6641A D.C. power supply was used, obtained from Hewlett-Packard Co. located in Loveland, Colo. A multi-function I/O electronic controller, obtained from Hewlett Packard, and an IBM Pentium II PC were also used.

The syringe pump and the D.C. power supply received input signals from the I/O electronic controller, which received signals from the PC. Unless otherwise indicated, the syringe pump infusion rate was 0.3 ml/min. The aerosol generation time was 10 seconds and the delivery volume was 50 ml. The mass delivery rate was 5.2 mg/sec. The average temperature of the capillary during aerosol formation was maintained between the boiling point of the liquid and 400° C.

The MMADs of the generated aerosols were measured using a MOUDI cascade impactor Model 100, obtained from MSP Corp. located in Minneapolis, Minn. An adapter was used to connect the capillary holder to a 90° angle induction port fixed atop a MOUDI cascade impactor. A United States Pharmacopeia standard induction port USP (2000) was employed together with the adapter. The adapter had a circular cross-section with holes placed circumferentially around the capillary to provide air inflow into the induction port. Aluminum foil was used as the substrate for the top nine stages of the impactor, and the lowest stage consisted of a Type A/E glass fiber after-filter, obtained from Gelman Sciences located in Ann Arbor, Mich.

The cascade impactor was operated according to the manufacturer's specifications. The impactor was operated at an air flow rate of 30 liters per minute with flow into the open end of USP induction port and a total aerosol production of less than 100 mg. A loading of 30 to 60 mg total aerosol mass in the impactor gave fairly consistent results. The nine stages and the after-filter were weighed before and after aerosol capture, using a Model AP250D analytical balance, obtained from Ohaus Corp. located in Florham Park, N.J. The solid component particle size distributions were determined by quantifying the mass of solute on each stage by washing the aluminum foils and the after-filter with a pre-determined volume of methanol and using a high performance liquid chromatography (HPLC) assay. All experiments were performed in replicate (n≧5) and results are presented as mean (sample standard deviation).

The particle size distributions of the solid component and the total aerosol of each sample were calculated using scientific graphing software SigmaPlot Version 3.0, obtained from Jandel Corp. located in San Rafael, Calif. The software used a least-squares, non-linear regression method to fit the impactor data to a log-normal curve.

Certain abbreviations or terms used within the examples are set forth below. Other abbreviations used, unless otherwise indicated, have the meaning set forth elsewhere herein, or the ordinary meaning in the art.

| | |
|---|---|
| BUD = | budesonide |
| BZ = | benzil |
| DEG = | diethylene glycol |
| DMSO = | dimethyl sulfoxide |
| DPG = | dipropylene glycol |
| DOC = | deoxycorticosterone |
| EG = | ethylene glycol |
| FORM = | formamide |
| GSD = | geometric standard deviation |
| MMAD = | mass median aerosol diameter |
| OA = | oleyl alcohol |
| PG = | propylene glycol |
| PhS = | phenyl salicylate |
| TEG = | triethylene glycol |
| TetEG = | tetraethylene glycol |

1. Effect of Solid Component Concentration on Solid Component MMAD

Solutions were formed by dissolving different amounts of various solid components in a liquid component. This solution was aerosolized using the aerosol generator described above and the MMAD of the material and the aerosol were measured using the cascade impactor described above to observe the effects of the concentration of the solid component on the MMAD of the solid component.

In the examples, it was attempted to make the particle size distribution of the solid component aerosol particles similar or approximately equal to the particle size distribution of the aerosol. More particularly, it was attempted to make the ratio of the solid component MMAD to the total aerosol MMAD greater than or equal to about 0.75. Although these particular examples were directed to achieving a particular particle size distribution, Applicants note that other particle size distributions may be desirable in different applications. In addition, some of the examples exhibit an increase in the degree of uniformity of the particle size distribution. The present invention is not limited to methods which achieve a particle size distribution of the solid component that is similar or approximately equal to the particle size distribution of the aerosol or a particle size distribution that is perfectly uniform, and in fact can be used to achieve any predetermined particle size distribution of the material.

The BZ, DOC and PhS used in the examples were obtained from Sigma Chemical Co., located in St. Louis, Mo. The PG used in the examples was obtained from Fisher Scientific, located in Raleigh, N.C.

A. Budesonide in Propylene Glycol

Referring to Table 1, sample solutions having BUD concentrations of 0.05% and 0.10% yielded BUD/aerosol MMAD ratios of 0.96 and 0.86, respectively. The mixture having a 0.5% BUD concentration, however, yielded a BUD/aerosol MMAD ratio of less than 0.75. This indicates that employing a sufficiently low concentration of BUD in a PG vehicle were effective for achieving the desired BUD and PG particle size distributions.

TABLE 1

| BUD concentration in PG (%) | Aerosol MMAD (μm) | BUD MMAD (μm) | BUD GSD | BUD/Aerosol MMAD ratio |
|---|---|---|---|---|
| 0 | 1.65 | — | — | — |
| 0.05 | 1.14 | 1.09 | 2.42 | 0.96 |
| 0.10 | 0.95 | 0.82 | 2.96 | 0.86 |
| 0.50 | 0.82 | 0.47 | 3.22 | 0.57 |

B. Deoxycorticosterone in Propylene Glycol

The desired particle size distributions of solutions formed of DOC and PG were achieved by reducing the DOC concentration in the mixture. In this example, the flow rate of the solution was 0.3 ml/min (5.2 mg/sec).

Referring to Table 2, sample solutions having DOC concentrations of 0.03125%, 0.0625%, 0.125% and 0.25% yielded DOC/aerosol MMAD ratios of 1.02, 1.02, 1.02, 0.95, respectively. Thus, the desired particle size distribution was achieved in these samples. The desired particle size distribution was not achieved in the mixtures having 0.5% and 1.0% DOC concentrations yielded DOC/aerosol MMAD ratios of 0.69 and 0.60, respectively. In addition, the GSD of the aerosols having a DOC concentration of 0.25% and 0.5% were relatively high, indicating a polydispersed particle size distribution. A monodispersed particle size distribution was achieved in solutions containing lower amounts of DOC, i.e., 0.03125%, 0.0625% and 0.125% DOC in PG.

TABLE 2

| DOC concentration in PG (%) | Aerosol MMAD (μm) | DOC MMAD (μm) | DOC GSD | DOC/Aerosol MMAD ratio |
|---|---|---|---|---|
| 0 | 1.65 | — | — | — |
| 0.03125 | 1.69 | 1.73 | 1.43 | 1.02 |
| 0.0625 | 1.47 | 1.50 | 1.46 | 1.02 |
| 0.125 | 1.23 | 1.26 | 1.63 | 1.02 |
| 0.25 | 1.06 | 1.01 | 3.41 | 1.05 |
| 0.5 | 0.85 | 0.59 | 3.29 | 0.69 |
| 1.0 | 0.68 | 0.41 | 2.57 | 0.60 |

Figure 3:
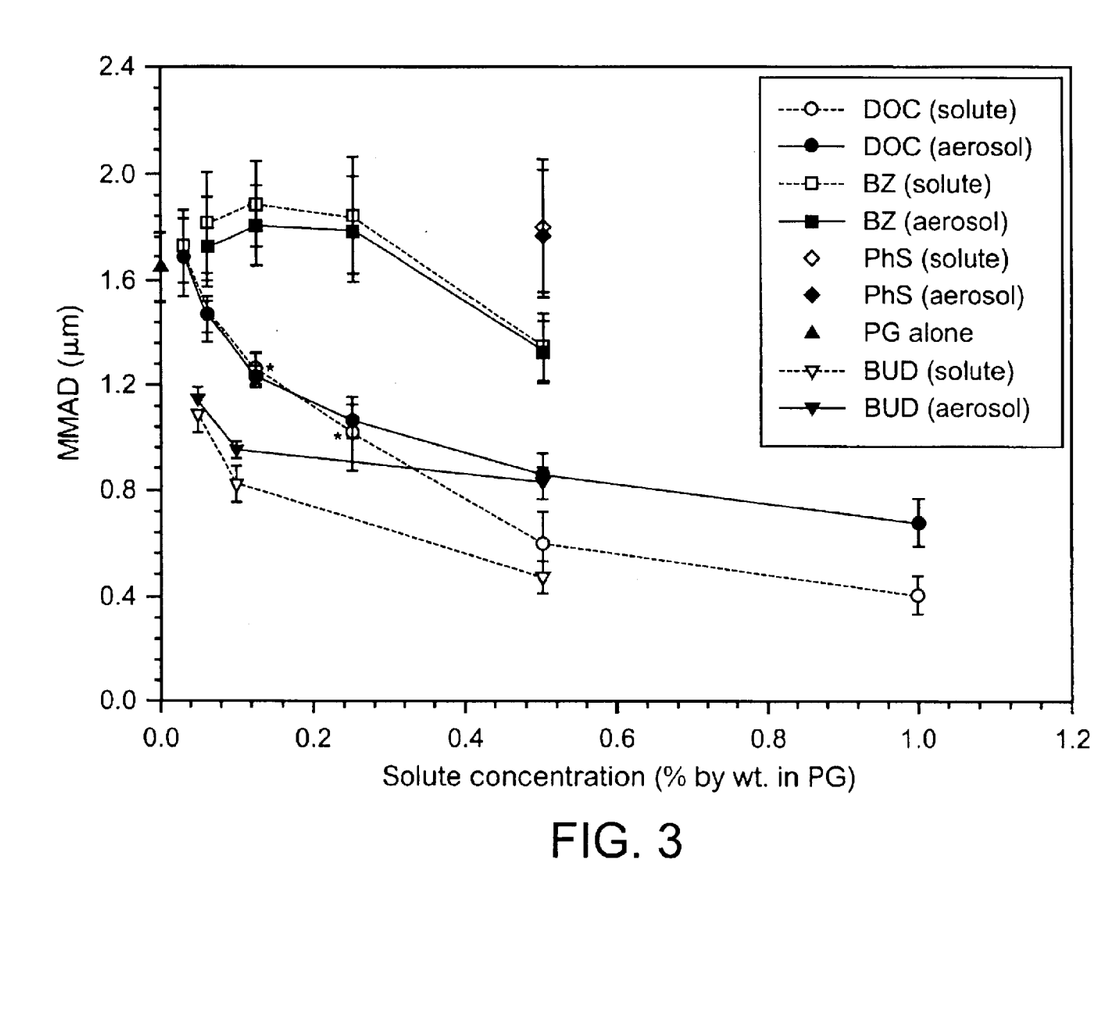
FIG. 3 is a graph of the solute and aerosol MMADs of aerosols formed from solutions of deoxycorticosterone and propylene glycol, benzil and propylene glycol, phenyl salicylate and propylene glycol, and budesonide and propylene glycol, as a function of the solute concentration, according to an exemplary embodiment of the present invention.

It can be seen that employing a sufficiently low concentration of DOC in a propylene glycol vehicle can be effective for achieving the desired particle size distribution of DOC. The solution containing 0.03125% DOC had a DOC MMAD that was approximately equal to the MMAD of the aerosol. However, solutions having higher DOC concentrations exhibited decreased aerosol MMAD values. Solutions having higher DOC concentrations also had decreased DOC MMAD values in comparison with the DOC MMAD of the mixture containing 0.03125% DOC. The first component and aerosol MMAD values of BUD, DOC, BZ and PhS in PG are set forth in FIG. 3.

C. Benzil and Phenyl Salicylate in Propylene Glycol

Mixtures containing various concentrations of BZ and 0.5% PhS in PG were aerosolized in order to observe the effects of solute concentration on the solute and aerosol MMAD values of each mixture. The solute and aerosol MMAD values of each mixture are set forth in Table 3:

TABLE 3

| BUD concentration in PG (%) | Aerosol MMAD (μm) | Solute MMAD (μm) | BZ GSD | Solute/Aerosol MMAD ratio |
|---|---|---|---|---|
| 0 | 1.65 | — | — | — |
| 0.0625 | 1.73 | 1.82 | 1.52 | 1.05 |
| 0.125 | 1.81 | 1.89 | 1.52 | 1.04 |
| 0.25 | 1.79 | 1.84 | 1.50 | 1.03 |
| 0.5 | 1.32 | 1.34 | 1.46 | 1.02 |
| 0.5 PhS/PG | 1.77 | 1.80 | 1.42 | 1.02 |

As can be seen from Table 3, the aerosol MMAD of the mixtures containing 0.0625%, 0.125% and 0.25% BZ were comparable to the aerosol MMAD of pure PG. The BZ MMAD values of the mixtures containing 0.0625%, 0.125% and 0.25% BZ were 1.82, 1.89 and 1.84 μm respectively. The BZ/aerosol MMAD ratio for the BZ/PG mixtures ranged between 1.02 and 1.05 over the range of solute concentrations tested. The BZ/aerosol MMAD ratio of the mixture having a PhS concentration of 0.5% was 1.02. Thus, co-condensation was achieved in these BZ and PhS mixtures in PG, respectively, even at these relatively high concentrations. This can be attributed to the fact that BZ and PhS are considerably more volatile than DOC. While not wishing to be bound by theory, Applicants believe that co-condensation may be difficult or impossible to achieve above certain critical first component concentrations. These critical values are generally specific to the first component and liquid component which are employed.

2. Effect of Liquid Component Boiling Point on Solid Component MMAD

Increasing the solute/aerosol MMAD ratio and achieving substantial monodispersity for solid components having low volatilities, such as DOC, can be achieved by using liquid components which have relatively high boiling points. Several sample solutions were prepared by adding a constant amount of DOC (0.5% w/w) to various liquids to determine the effect of the boiling point of the liquid on the DOC/aerosol MMAD ratio and the solute GSD.

Referring to Table 4, DOC/liquid solutions were formed using propylene glycol and liquids that have a higher boiling point than propylene glycol. Upon aerosolization, these solutions yielded DOC/aerosol MMAD ratios of 0.93, 0.95, 0.96, 1.06, 1.13 and 1.02 for EG, DPG, DEG, TEG, TetEG and OA, respectively. The particle size distributions of the aerosols formed of DPG, DEG, TEG, TetEG and OA were substantially uniform. In comparison, a solution of DOC (0.5% w/w) in PG and DMSO yielded a DOC/total aerosol MMAD ratio of less than 0.75. Employing a liquid with a sufficiently high boiling point was effective for achieving the predetermined and substantially monodispersed particle size distribution of the deoxycorticosterone in the solution.

TABLE 4

| 0.5%$^{w}/_{w}$ DOC in different solvents | Aerosol MMAD (μm) | Solute MMAD (μm) | Solute GSD | Solute/Aerosol MMAD ratio |
|---|---|---|---|---|
| PG (boiling point: 188° C.) | 0.85 | 0.59 | 3.29 | 0.68 |
| DMSO (189° C.) | 1.17 | 0.03 | 2.34 | 0.03 |
| EG (198° C.) | 1.08 | 1.01 | 2.87 | 0.93 |
| FORM (210° C.) | 0.57 | 0.35 | 2.22 | 0.62 |
| DPG (232° C.) | 0.78 | 0.75 | 1.82 | 0.95 |
| DEG (245° C.) | 0.98 | 0.95 | 2.08 | 0.96 |
| TEG (288° C.) | 0.45 | 0.48 | 1.94 | 1.06 |
| TetEG (326° C.) | 0.61 | 0.69 | 2.12 | 1.13 |
| OA (333° C.) | 0.29 | 0.30 | 1.47 | 1.02 |

DMSO and FORM, each of which have boiling points that are higher than that of PG, yielded DOC/aerosol MMAD ratios (0.03 and 0.62, respectively) which were less than the DOC/aerosol MMAD ratio of PG. While not wishing to be bound by theory, Applicants believe that other characteristics of the liquid such as, for example, the chemical structure, had an effect on the solute and aerosol MMADs.

Figure 4:
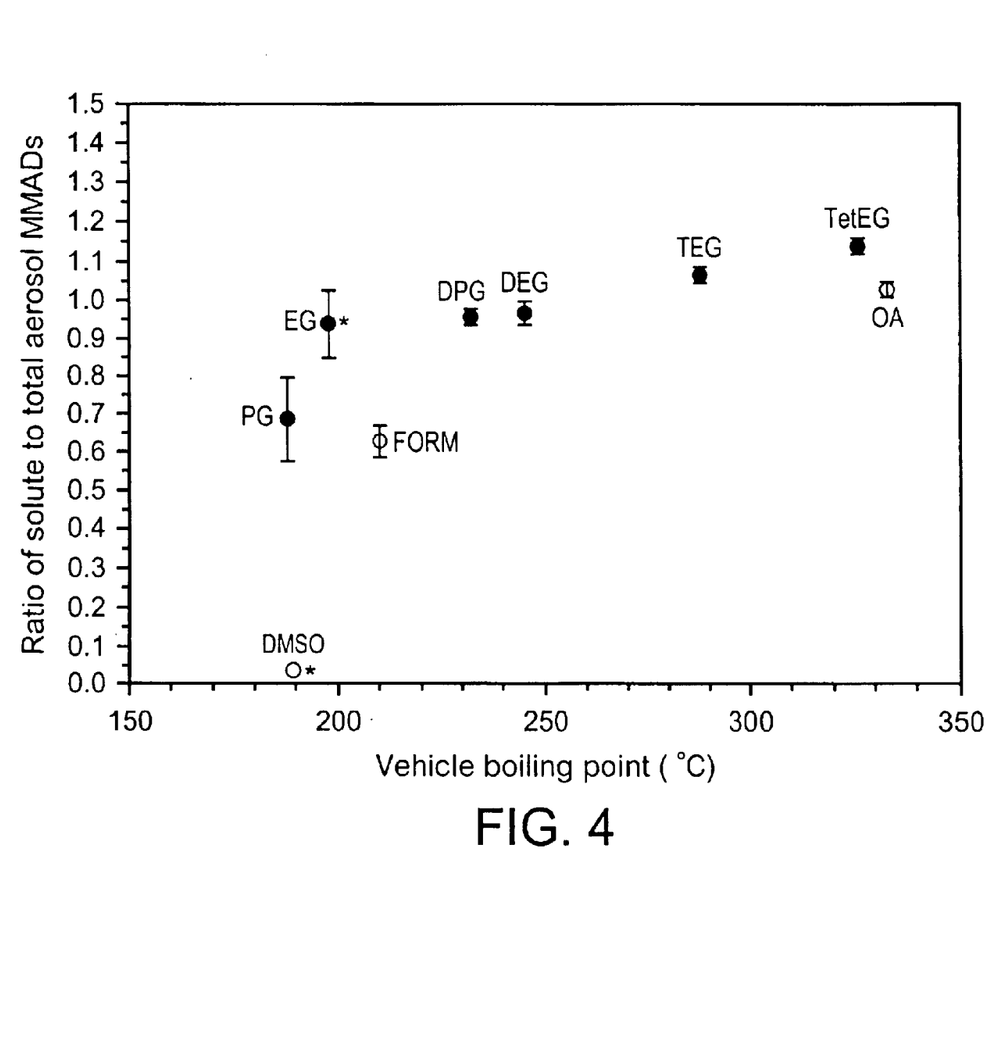
FIG. 4 is a graph of the deoxycorticosterone/aerosol MMAD ratios of aerosols formed from solutions of deoxycorticosterone and various liquids, as a function of the liquid boiling point, according to an exemplary embodiment of the present invention.

FIG. 4 shows a graph of the DOC/total aerosol ratio as a function of the liquid component boiling point. It is apparent from FIG. 4 that using a liquid component having an increased boiling point generally had the effect of increasing the solute/aerosol MMAD ratio.

Those skilled in the art will recognize that some medicaments may benefit from CAG aerosolization and inhalation without co-condensation with the vehicle. For example, aerodynamic particle sizes substantially less than 0.5 μm, such as about 0.1 or 0.2 μm, are known to be deposited homogeneously by aerosol particle diffusion in the extreme lung periphery. It is feasible that some medicaments when deposited in such very small sizes from aerosols having vehicles with a greater MMAD may exhibit substantially different pharmaceutical and pharmacological or toxicological properties than medicaments with a MMAD similar to those of the vehicle.

While this invention has been illustrated and described in accordance with preferred embodiments, it is recognized that variations and changes may be made without departing from the invention as set forth in the claims.

What is claimed is:

1. A method for generating an aerosol, comprising the steps of:

preparing a solution comprising a first component in a liquid component such that after volatilization of the liquid component, an aerosol is formed wherein the aerosol comprises at least first component aerosol particles and liquid component aerosol particles, and the first component aerosol particles have a predetermined particle size distribution, wherein the solution is prepared such that the amount of the first component therein is sufficient to achieve the predetermined particle size distribution; and passing the solution through a flow passage while heating the solution to a temperature sufficient to volatilize the liquid component, wherein the flow passage comprises an outlet through which the first component and the volatilized liquid component flow, and wherein the aerosol particles are formed.

2. The method according to claim 1, wherein the solution is prepared such that the amount of the first component therein is sufficient to achieve a predetermined ratio of the mass median aerosol diameter of the first component aerosol particles to the mass median aerosol diameter of the liquid component aerosol particles.

3. The method according to claim 2, wherein the first component is present in an amount effective to cause the ratio of the mass median aerosol diameter of the first component aerosol particles to the mass median aerosol diameter of the liquid component aerosol particles to be greater than or equal to about 0.75 after formation of the aerosol.

4. The method according to claim 3, wherein the first component is present in an amount effective to cause the mass median aerosol diameter of the first component aerosol particles and the mass median aerosol diameter of the liquid component aerosol particles to be approximately equal after formation of the aerosol.

5. The method according to claim 2, wherein the first component is present in an amount effective to cause the ratio of the mass median aerosol diameter of the first component aerosol particles to the mass median aerosol diameter of the liquid component aerosol particles to be less than or equal to about 0.75 after formation of the aerosol.

6. The method according to claim 1, wherein the flow passage is of capillary dimensions which permit volatilization of substantially all of the liquid component when the solution is passed through the flow passage while heating.

7. The method according to claim 1, wherein the solution comprises the first component in the form of solid particles dissolved in the liquid component.

8. The method according to claim 1, wherein at least some of the first component is volatilized during the heating of the solution.

9. The method according to claim 8, wherein the volatilized liquid component and the volatilized first component condense after mixing with ambient air to form the aerosol.

10. The method according to claim 1, wherein the first component comprises a medicament suitable for treating a respiratory ailment.

11. The method according to claim 1, wherein the first component is budesonide.

12. The method according to claim 1, wherein the solution comprises the first component in a concentration of less than about 0.5% by weight.

13. The method according to claim 12, wherein the solution comprises the first component in a concentration of less than about 0.1% by weight.

14. The method according to claim 1, wherein the liquid component is selected from the group consisting of water, propylene glycol, ethylene glycol, dipropylene glycol, diethylene glycol, triethylene glycol, tetraethylene glycol, oleyl alcohol, ethanol, and mixtures thereof.

15. The method according to claim 1, wherein the aerosol is deposited into a lung of an animal or human.

16. The method according to claim 1, wherein the first component flows out of the outlet of the flow passage contemporaneously with the volatilized liquid component.

17. The method according to claim 1, wherein the mass median aerosol diameter of the first component aerosol particles is from about 0.3 to 2 µm.

18. The method according to claim 1, wherein the solution is prepared such that the amount of the first component therein is sufficient to achieve a substantially monodispersed particle size distribution of the first component aerosol particles.

19. The method according to claim 18, wherein the geometric standard deviation of the particle size distribution of the first component is less than or equal to about 2.

20. The method according to claim 1, wherein the first component is selected from the group consisting of budesonide, albuterol, deoxycorticosterone, benzil, phenyl salicylate, and mixtures thereof.

21. A method for generating an aerosol, comprising the steps of:
preparing a solution comprising a first component in a liquid component such that after volatilization of the liquid component, an aerosol is formed wherein the aerosol comprises at least first component aerosol particles and liquid component aerosol particles, and the first component aerosol particles have a substantially monodispersed particle size distribution, wherein the solution is prepared such that the boiling point of the liquid component is sufficient to achieve the substantially monodispersed particle size distribution; and
passing the solution through a flow passage while heating the solution to a temperature sufficient to volatilize the liquid component, wherein the flow passage comprises an outlet through which the first component and the volatilized liquid component flow, and wherein the aerosol particles are formed.

22. The method according to claim 21, wherein the flow passage is of capillary dimensions which permit volatilization of substantially all of the liquid component when the solution is passed through the flow passage while heating.

23. The method according to claim 21, wherein the solution comprises the first component in the form of solid particles dissolved in the liquid component.

24. The method according to claim 21, wherein at least some of the first component is volatilized during the heating of the solution.

25. The method according to claim 24, wherein the volatilized liquid component and the volatilized first component condense after mixing with ambient air to form the aerosol.

26. The method according to claim 21, wherein the first component comprises a medicament suitable for treating a respiratory ailment.

27. The method according to claim 21, wherein the first component is budesonide.

28. The method according to claim 21, wherein the solution comprises the first component in a concentration of less than about 0.5% by weight.

29. The method according to claim 28, wherein the solution comprises the first component in a concentration of less than about 0.1% by weight.

30. The method according to claim 21, wherein the liquid component is selected from the group consisting of water, propylene glycol, ethylene glycol, dipropylene glycol, diethylene glycol, triethylene glycol, tetraethylene glycol, oleyl alcohol, ethanol, and mixtures thereof.

31. The method according to claim 21, wherein the aerosol is deposited into a lung of an animal or human.

32. The method according to claim 21, wherein the first component flows out of the outlet of the flow passage contemporaneously with the volatilized liquid component.

33. The method according to claim 21, wherein the mass median aerosol diameter of the first component aerosol particles is from about 0.3 to 2 µm.

34. The method according to claim 21, wherein the geometric standard deviation of the particle size distribution of the first component is less than or equal to about 2.

35. A method for generating an aerosol, comprising the steps of:
preparing a solution comprising a first component in a liquid component such that after volatilization of the liquid component, an aerosol is formed wherein the aerosol comprises at least first component aerosol particles and liquid component aerosol particles, and the first component aerosol particles have a predetermined and substantially monodispersed particle size distribution, wherein the solution is prepared such that the amount of the first component therein and the boiling point of the liquid component are sufficient to achieve the predetermined and substantially monodispersed particle size distribution; and passing the solution through a flow passage while heating the solution to a temperature sufficient to volatilize the liquid component, wherein the flow passage comprises an outlet through which the first component and the volatilized liquid component flow, and wherein the aerosol particles are formed.

36. A method for controlling particle size distribution of an aerosol, comprising:

preparing a solution comprising a first component in a liquid component such that the solution achieves a predetermined particle size distribution of first component aerosol particles upon volatilization of the solution by passing the solution through a flow passage while heating the solution.

37. The method according to claim 36, wherein the concentration of the first component is selected to achieve the predetermined particle size distribution of the first component aerosol particles.

38. The method according to claim 36, wherein the boiling point of the liquid component is selected to achieve the predetermined particle size distribution of the first component aerosol particles.

39. The method according to claim 36, wherein the first component is a medicament.

40. A method for providing a monodispersed particle size distribution of an aerosol, comprising:

preparing a solution comprising a first component in a liquid component, such that the solution achieves a monodispersed particle size distribution of first component aerosol particles, upon volatilization of the solution by passing the solution through a flow passage while heating the solution.

41. The method according to claim 40, wherein the concentration of the first component is selected to achieve the monodispersed particle size distribution of the first component aerosol particles.

42. The method according to claim 40, wherein the boiling point of the liquid component is selected to achieve the monodispersed particle size distribution of the first component aerosol particles.

43. The method according to claim 40, wherein the first component is a medicament.

44. A method for generating an aerosol, comprising the steps of:

(a) preparing a liquid mixture comprising a first component and a liquid component such that after volatilization of the liquid component, an aerosol is formed, wherein the aerosol comprises at least first component aerosol particles and liquid component aerosol particles and the first component aerosol particles have a predetermined and substantially monodispersed particle size, wherein the liquid mixture is prepared to achieve the predetermined and substantially monodispersed particle size by adjusting the concentration of the first component in the liquid component, by adjusting the boiling point of the liquid component, or combinations thereof, and (b) passing the liquid mixture through a flow passage while heating the liquid mixture to a temperature sufficient to volatilize the liquid component, wherein the flow passage comprises an outlet through which the first component and the volatilized liquid component flow, and wherein the aerosol particles are formed.

45. The method according to claim 44, wherein the liquid mixture is a suspension or a solution.

* * * * *